Figures 1, 2:
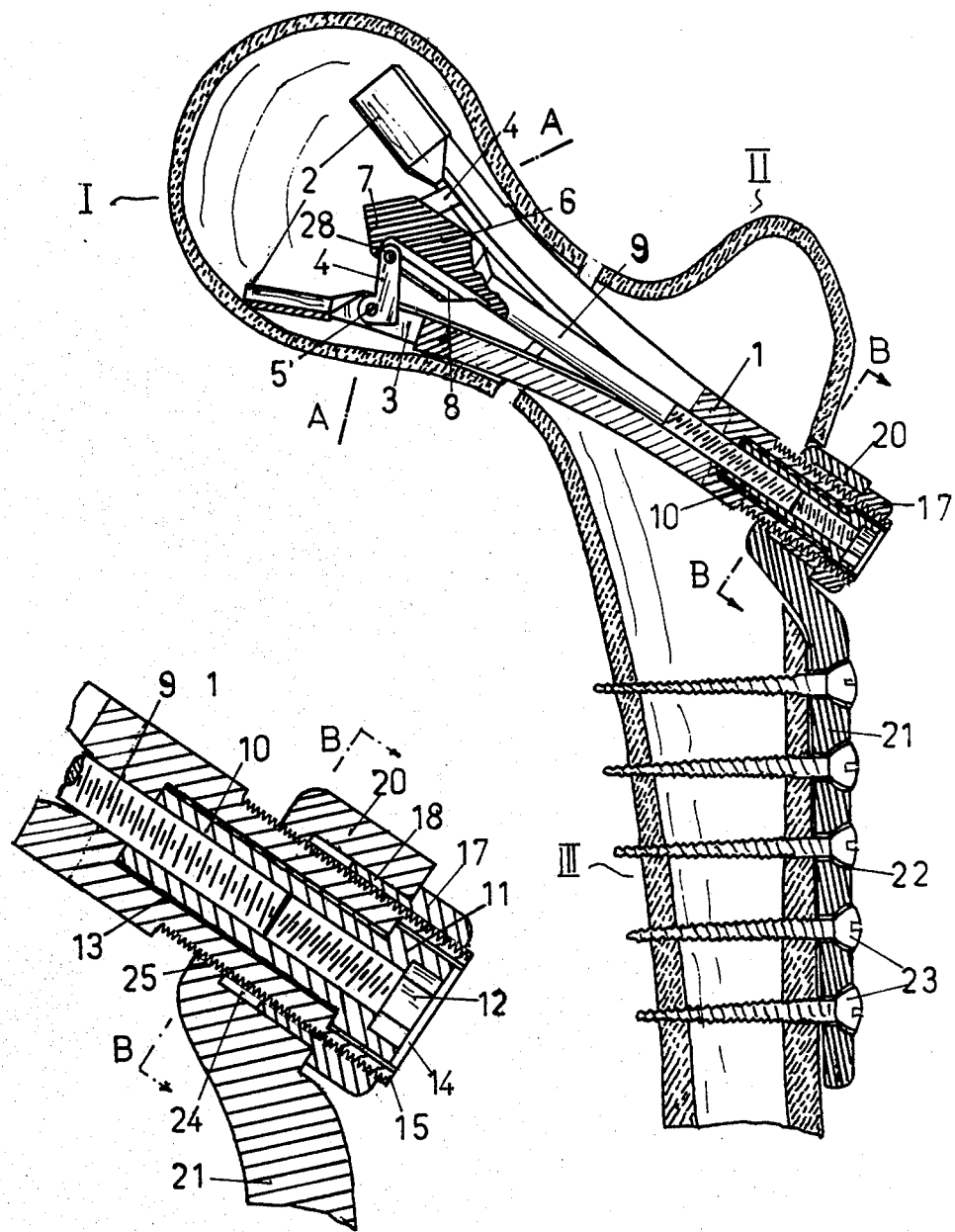

United States Patent [19]

Aginsky

[11] 4,236,512
[45] Dec. 2, 1980

[54] CONNECTOR FOR FRACTURED BONES

[76] Inventor: Jacob Aginsky, 18 Rachel St., Haifa, Israel

[21] Appl. No.: 5,103

[22] Filed: Jan. 22, 1979

[30] Foreign Application Priority Data

Feb. 12, 1978 [IL] Israel .......................................... 54025

[51] Int. Cl.³ ........................... A61F 5/04; A61B 17/18
[52] U.S. Cl. ................................................. 128/92 BA
[58] Field of Search ......... 128/92 BA, 92 BB, 92 BC, 128/92 R, 92 D

[56] References Cited

U.S. PATENT DOCUMENTS

| | | | |
|---|---|---|---|
| 2,699,774 | 1/1955 | Livingston ...................... | 128/92 BB |
| 3,678,925 | 7/1972 | Fisher et al. ..................... | 128/92 BB |
| 3,759,257 | 9/1973 | Fisher et al. ..................... | 128/92 BC |

FOREIGN PATENT DOCUMENTS

| | | | |
|---|---|---|---|
| 2701279 | 7/1977 | Fed. Rep. of Germany ...... | 128/92 BC |
| 1436546 | 5/1976 | United Kingdom ............... | 128/92 BA |

*Primary Examiner*—Ronald L. Frinks

*Attorney, Agent, or Firm*—Schwartz, Jeffery, Schwaab, Mack, Blumenthal & Koch

[57] ABSTRACT

A connector for treatment of a fractured femur neck consists of an intramedullary nail to be inserted into the bone cavity through a bore made in the trochanter region. The leading or front end of the nail is provided with an expandable portion that can be urged against the cavity walls of the bone until it is held therein in a firm grip. This operation is carried out by manipulation of a screw in the rear portion of the nail which projects out of the bone by a short length. The rear end of the connector is fastened to the shaft of the femur by means of a flat fixator plate which is firmly fastened to the bone material by screws on the one hand, and to the connector by a socket adapted to be moved along the rear end by a screw-thread connection. The two fractured bone parts are drawn together and held in close attachment by pulling the fixator plate, together with the shaft portion towards the front end of the connector which has been expanded previously and clamps the neck in a firm grip.

4 Claims, 4 Drawing Figures

CONNECTOR FOR FRACTURED BONES

The invention relates to a connector for a fractured bone, in particular to a connector for use in case of subcapital, subtrochanteric and pertrochanteric fractures of the femur. It has been tried in the past to connect the broken fragments of bones by inserting into their cavity a nail or sleeve provided at its leading or front end with an expandable portion, and at its trailing or rear end—which is long enough to protrude out of the bone—with a compression disc and with means for pressing this disc against the bone end. The expandable portion is positioned in the flared-out end of the cavity, and by spreading the arms or branches against the cavity walls, the sleeve is secured in this bone portion. The fractured surfaces of the bone fragments are pressed together by applying pressure on the rear fragment by means of the said disc, usually by tightening a nut on the screw-threaded sleeve, until the fractured bone surfaces meet. The nail remains in the bone until callus forms and the two fragments have grown together into their former shape.

This treatment has been successfully applied to fractured long tubular bones, by using intramedullary compression nails of the kind described in my Israeli Patent Specifications Nos. 48826 and 53703. The use of these nails has proved particularly advantageous for the reason that the fractured bone fragments are connected in a completely rigid fashion, permitting the patient to walk a few days after the nail has been inserted and tightened.

Far more difficult to treat are fractures of the neck of the femur, in particular subcapital fractures which, up to the present, could not be firmly gripped by an expansion member and did require, in frequent cases, replacement of the head by an artificial spherical prosthesis. In the case of this type of fracture it has been tried to employ the same compression nail as used in long tubular bones, but of shorter length, as for instance, described in U.S. Pat. No. 3,678,925, Artur Fischer. The treatment using this kind of connector, however, is not successful if the patient is supposed to use the broken bone after a short time of rest, as has become possible in the case of operations of the femur using the above-mentioned compression nail. The reasons for this failure are: (1) the nail or connector cannot be firmly fixed in the cortex of the head, which is able to transmit the forces acting on the bone, but owing to the insufficient spreading of the expansion members it only grips the sponge filling the medullary cavity; this results in lateral and torsional movement of the connector and shifting of the joined bone ends as soon as a load is brought to bear on the head. (2) A straight compression connector is unsuitable for taking up the strong bending movement exerted on the bone by the weight of the patient which would either cause the fractured bone parts to separate at an angle or would lead to the destruction of the thin bone structure of the trochanter, through which the trailing end necessarily protrudes, and against which the disc has been pressed. The aforecited connector comprises, at its front end, an expandable portion in the form of segments or tongues of a longitudinally split sleeve, which are spread out by a wedge-shaped expander drawn in between these segments by the manipulation of a screw at the rear end of the device. After the segments or tongues have been sufficiently spread, a nut is tightened towards the trochanter region with the intention of drawing the fractured bone parts together. The method of spreading the tongues by means of a wedge is not satisfactory since for wide spreading the wedge has to be drawn far rearwards, whereby the ends of these tongues are being bent inwardly by the reaction forces of the cavity walls.

Instead of obtaining a concave contour to conform to the surface at the outer end of the femur head, these tongues are bent into convex shape, which gives the connector no hold in the cavity of the head of the femur. In addition, the inwardly bent tongue ends do not readily reach the bone cortex, but only the surrounding sponge which gives way under heavy stress and moments. The rear end of the connector described in the above-mentioned Patent bears against the bone material of the trochanter which is thin and not sufficiently resistant. As soon as bending stress is exerted the disc and the nut at the rear end tightened against the bone material from the outside will either break through the bone wall or will cause the expandable portion to slip partly out of the head cavity resulting in an angular displacement of the previously joined bone fragments. It has long been recognized that, when replacing the head of the femur by a metal prosthesis, this latter has to contain the entire neck portion and has to be inserted into the shaft of the femur, in order to withstand the strong bending moment exerted on the neck. This kind of support cannot be given by the cited compression nail which, therefore, can only be used in those cases, where no load is imposed on the fractured bone until it is completely healed.

With the intention to save, as far as possible, the original bone parts and to make them join by natural growth, instead of replacing them by an artificial ball joint with all its deficiencies, I have designed a connector for a fractured neck of a femur which should fulfil the following requirements: (1) When inserted into the head of the femur the expandable portion should be suitable for forceful expanding against the bone walls of the cavity of the femur head and for completely rigid connection between connector and the bone. (2) The rear end of the connector should permit its rigid connection to the femur shaft, instead of to the trochanter portion as hitherto proposed. (3) The connector should be constructed to be of sufficient rigidity to withstand the stresses exerted by standing or walking of the patient, so as to permit his leaving the sick bed and his walking without crutches soon after the operation. In addition the connector should compress the fractured surfaces continuous so as to hasten the healing process, while the patient can be active.

With these objects in view I have designed a connector for a fractured femur neck which comprises:

a sheath adapted to be inserted with its leading or front end through a bore made in the trochanter region, into the cavity of the femur head, the sheath being of a length sufficient to protrude out of said bore by a short length of its trailing or rear end, said front end being shaped to form at least three resilient tongues adapted to be forcefully expanded in outward direction toward the cavity walls, while its rear end is provided with outer screw thread interrupted by at least one flat surface extending along the sheath for a length not less than the length of the thread, expander means adapted to be operated from the rear end of said sheath for either expanding or re-closing said tongues, a shaft fixator comprising a flat plate provided with perforations for attaching this plate to the femur shaft by means of screws, said plate being integrally connected to a socket provided with an opening corresponding in shape and size to the cross section of said flattened rear end of said sheath, the axis of said socket opening and said plate surface adjacent the femur shaft forming an angle of 126°+10°, said socket being adapted to be moved along said sheath and to be biased against the outer bone surface by means of an internally threaded nut movable on said screw threaded sheath end.

In a preferred embodiment of the connector the expanding mechanism adapted to spread the said three or more resilient tongues, consists of an expander head in the form of a cylinder attached to the front end of a bar movable inside and along the sheath of the connector, which cylinder is provided with three or more pivots each holding the front end of a radially outswinging link, the rear end of which link is connected to a pivot near the front end of one of the tongues, both pivots of each link being parallel. Rearward movement of the expander head forces the links and the tongues attached thereto sideways and outwards, pressing the tongues against the cavity walls. The longitudinal movement of the said bar is attained by rotation of an internally threaded sleeve axially fixed in the rear end of the sheath engaging with an outer screw thread on the end of the bar, this sleeve being rotated by a tool inserted into a suitably shaped recess in its rear end.

The sheath is, at its rear end, preferably provided with two opposed flat surfaces which engage with an oblong opening in the socket of the shaft fixator, preventing the rotation of the sheath relative to said shaft fixator and to the thereto-connected bone parts.

Figure 3:
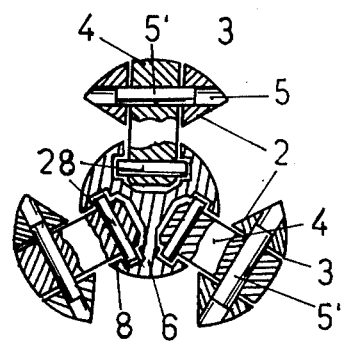
Figure 4:
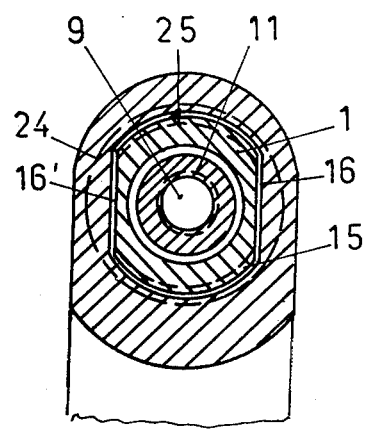

In the accompanying drawing which illustrates, by way of example, one embodiment of the invention, FIG. 1 is a longitudinal section through the upper part of a femur and through the connector holding the fractured bone in position, FIG. 2 is an enlarged section of the rear portion of the connector sheath and of the socket of the shaft fixator, FIG. 3 is a section along A—A of FIG. 1, and FIG. 4 is a section along B—B of FIGS. 1 and 2.

FIG. 1 illustrates a fracture through the neck of a femur which, for reasons of clarity, is shown before its final compression by the connector. It can be visualised that the spherical head I is held by the expandable front portion of the connector, that the trochanter region II is perforated by drilling a hole for receiving the rear end of the connector as well as a portion of the shaft fixator socket, the latter being screwedly connected to the femur shaft III. The connector as depicted in FIGS. 1 to 4 consists of an outer sheath 1 which is split into three tongues 2 by longitudinal slots beginning from the front end. Each tongue is slotted, near its front end, by a through-going recess 3 and drilled at right angles to this recess by a bore 5. The rear end of one link 4 each is positioned in the recess 3 and hingedly connected to the tongue by a pin 5'. The front ends of the tongues are hollowed out to permit a cylindrical expander head to be accommodated between the tongues in non-expanded state. The above-mentioned expander head is in the form of a cylinder pointed at its front end 7 for easy penetration into the sponge material of the bone; it is provided with three longitudinal slots 8 in its periphery, of a width slightly wider than the thickness of the links 4, which slots accommodate the three links and hold them pivotally attached by pins 28 protruding on each side of the links. The expander head is integral with a bar 9 provided with screw thread at its rear end which engages with an internally threaded sleeve 10. The sleeve 10 is widened at its rear end to form a collar 11 and a hexagonal recess 12 in the end surface of the collar. The sleeve is freely rotatable in an axial bore 13 in the rear portion of the sheath, which bore is widened at its rear end (14) to receive the collar 11.

The outside of the sheath is screw-threaded (15) and is flattened on opposite sides by two longitudinal flat sufaces 16 and 16' which serve two purposes as will be described hereinafter. A hexagonal nut 17 is continued in its front portion in the form of a tube 18 likewise provided with inner thread and is adapted to be tightened on to the threaded rear end of the sheath 1.

A shaft fixator consists of a socket 20 and a flat fixator plate 21 provided with perforations 22 for its fixation to the femur shaft III by screws 23. The socket is perforated by a circular bore 24 in its rear part and by an oblong hole 25 in its frontal section, the hole 25 corresponding to the cross section of the flattened rear portion of the sheath. The axis of the bore 24 and the flat plate 21 form between them an angle of 126° which corresponds to the angle at which the femur neck joins the shaft. This angle can deviate up to 10° in either direction (116°–136°), but in most cases the angle of 126° will fit the bone structure.

For treatment of a fractured femur neck the connector is driven into the head I through the aforementioned hole in the trochanter region. The connector end, which protrudes slightly out of the bone, is gripped by a spanner engaging with the flat surfaces 16 and 16', and an Allen key is inserted into the hexagonal recess 12 and the sleeve 10 is rotated therewith. This rotation pulls the threaded bar 9 and the expander head 8 to the rear whereby the tongues 2 are forcefully spread against the cortex wall of the head. Owing to their elasticity the tongues are bent in the form of parabolas which adhere to the bone and clamp it firmly. The rotation of the sleeve and the expansion of the tongues is preferably carried out with the aid of a torque wrench attached to the Allen key which is adjusted to a moment which is sufficient to grip the head but not too large so as to exert an excess pressure on the relatively brittle bone which may burst if overstressed. Now the socket 20 of the shaft fixator is slipped over the sheath end, the nut 17, 18 is threaded on the sheath and is tightened against the socket face which in turn presses on the bone in the trochanter region until the fractured parts meet and their fractured surfaces are matched. Screws 23 are now driven into the shaft through the holes 22, until the plate 21 is firmly connected thereto, and the nut 17 is again tightened to provide an absolutely rigid support for the fractured bone parts, permitting the patient to use the damaged leg a few days after insertion of the connector, and to place his full weight on the hip. After healing of the bone the connector is removed by first releasing the shaft fixator plate and afterwards unscrewing the nut, permitting the stripping of the shaft fixator. Now, by holding the sheath end in a spanner, the tongues are brought back into their original position by rotating the sleeve 10 and pushing the expander head forward; this releases the hold of the connector on the femur head, and the connector can now be withdrawn in a manner known to the art.

Although only one embodiment of the connector has been described and illustrated hereinbefore, it is understood that it may undergo many alterations and variations to be carried out by a person skilled in the art. This applies to the body of the sheath and to the shaft fixator, as well as to the movable parts, particularly to the mechanism for drawing the expander head rearwardly.

Any other kind of expansion mechanism may be employed with this connector for gripping the inside of the femur head, provided the expandable members are sufficiently resilient to assume a parabolic or otherwise curved shape which can hug the cavity's inner contours.

The expansion mechanism illustrated in FIGS. 1 to 3 is of the kind described and claimed in my Israeli Patent Specification No. 53703. This expansion mechanism is suitable for all intramedullary nails, both of the compression and the retraction type, to be used for fixation of long tubular bones; it is in particular, highly suitable in the treatment of femur neck fractures, wherein the difficulty of gripping the head firmly has, up to now, led to its frequent replacement by a prosthesis. The main surgical progress achieved by the present connector is in the fact that the shaft fixator takes care of the rigid angular fixation of the bone fragments while the non-rotatable sheath holds the parts fixed against radial displacement. The bone parts are, by these means, rigidly held together without, however, stressing the fracture itself, since the weight of the patient is transmitted by the connector direct from the femur shaft to the hip, thus facilitating the healing process.

I claim:

1. A connector for treatment of a fractured femur neck comprising:

a sheath adapted to be inserted with its leading or front end through a bore made in the trochanter region, into the cavity of the femur head, the sheath being of a length sufficient to protrude out of said bore by a short length of its trailing or rear end, said front end being shaped to form at least three resilient tongues adapted to be forcefully expanded in an outward direction toward the cavity walls, by means of an expander head attached to the front end of a bar movable inside and along said sheath, said expander head being provided with three pivots, one pivot each being positioned opposite each of said tongues, each pivot holding the front end of a radially outswinging link, the rear end of said link being connected to a pivot positioned in the front end of the respective tongue, parallel to the pivot in said expander head, the rear of said sheath being provided with external screw threads interrupted by at least one flat surface extending along the sheath for a length not less than the length of the thread, means for moving said bar and said expander head in an axial direction, said means being provided at the rear end of said sheath, a shaft fixator comprising a flat plate provided with performations for attaching said plate to the femur shaft by means of screws, said plate being integrally connected to a socket provided with an opening corresponding in shape and size to the cross section of said flattened rear end of said sheath including an internally threaded nut mounted on said flattened end, the axis of said socket opening and said plate surface adjacent the femur shaft forming an angle of 116°–136°, said socket being adapted to be moved along said sheath and to be biased against the outer bone surface by means of said internally threaded nut movable on said screw-threaded sheath end.

2. A connector as defined in claim 1, wherein said expander head is rigidly connected to a bar provided with screw thread on its rear portion, which bar engages with a sleeve provided with corresponding internal thread, said sleeve being freely rotatable in the rear portion of said sheath however fixed in axial direction, said sleeve being provided in its rear surface with a suitably formed recess for insertion of a manually operated spanner.

3. A connector for treatment of a fractured femur neck comprising:

a sheath adapted to be inserted with its leading or front end through a bore made in the trochanter region, into the cavity of the femur head, the sheath being of a length sufficient to protrude out of said bore by a short length of its trailing or rear end, said front end being shaped to form at least three resilient tongues adapted to be forcefully expanded in an outward direction toward the cavity walls, the rear of said sheath being provided with external screw threads interrupted by two longitudinally extending flat surfaces on opposite sides and extending along the sheath for a length not less than the length of the thread, expander means adapted to be operated from the rear end of said sheath for either expanding of reclosing said tongues, a shaft fixator comprising a flat plate provided with perforations for attaching said plate to the femur shaft by means of screws, said plate being integrally connected to a shaft fixator socket provided with an opening, the rear portion of which is cylindrical while the front portion is oblong corresponding to the shape of the rear end of said sheath and being of sufficient size to receive an internally threaded nut, the axis of said socket opening and said plate surface adjacent the femur shaft forming an angle of 116° to 136°, said socket being adapted to be moved along said sheath and to be biased against the outer bone surface by means of said internally threaded nut movable on said screw threaded sheath end.

4. A connector as defined in claim 1 or 3, comprising a nut the front portion of which is in the form of a cylinder adapted to be accommodated in the said rear portion of the opening in said shaft fixator socket, while its rear portion is shaped to form an external hexagon.

* * * * *